(12) United States Patent
Yang et al.

(10) Patent No.: US 11,065,170 B2
(45) Date of Patent: Jul. 20, 2021

(54) SMART MEDICAL REHABILITATION DEVICE

(71) Applicant: Hefei University of Technology, Hefei (CN)

(72) Inventors: Jiaoyun Yang, Hefei (CN); Ping Zhao, Hefei (CN); Lihong Zhu, Hefei (CN); Liang Zhang, Hefei (CN); Ning An, Hefei (CN); Ping Zhang, Hefei (CN)

(73) Assignee: HEFEI UNIVERSITY OF TECHNOLOGY, Hefei (CN)

( * ) Notice: Subject to any disclaimer, the term of this patent is extended or adjusted under 35 U.S.C. 154(b) by 339 days.

(21) Appl. No.: 15/815,554

(22) Filed: Nov. 16, 2017

(65) Prior Publication Data

US 2018/0133089 A1     May 17, 2018

(30) Foreign Application Priority Data

Nov. 17, 2016  (CN) .......................... 201611025862.5
Nov. 17, 2016  (CN) .......................... 201611026826.0

(51) Int. Cl.
*A61H 1/02*     (2006.01)
*A61B 5/11*     (2006.01)
(Continued)

(52) U.S. Cl.
CPC .......... *A61H 1/0262* (2013.01); *A61B 5/1118* (2013.01); *A61B 5/1122* (2013.01);
(Continued)

(58) Field of Classification Search
CPC .............. A63B 22/0664; A63B 22/067; A63B 22/0676; A63B 2022/0629;
(Continued)

(56) References Cited

U.S. PATENT DOCUMENTS 5,033,736 A * 7/1991 Hirschfeld ........... A61H 1/0214
                                                 482/57
5,976,083 A * 11/1999 Richardson .......... A61B 5/0245
                                                 482/8
(Continued)

*Primary Examiner* — Bradley H Philips
*Assistant Examiner* — Savannah L Gabriel
(74) *Attorney, Agent, or Firm* — Michael X. Ye; Morris, Manning & Martin, LLP

(57) ABSTRACT

A smart medical rehabilitation device comprises a driving unit, a linkage unit, a sensing unit and a rehabilitation evaluating unit that are mounted on a frame, wherein the linkage unit comprises a link mechanism and a slide mechanism linked thereto so that the slide mechanism can be moved together with the link mechanism, wherein the slide mechanism is driven by the driving unit to slide along the groove plate, the link mechanism is linked to move with the slide mechanism thus the link mechanism moves to the corresponding position so that the slide mechanism can assist a training object in performing lower limb rehabilitation training, and the rehabilitation evaluating unit evaluates the physical status and rehabilitation status of the training object according to the physiological information and exercise information of the same collected by the sensing unit, and adjusts the exercise frequency and the exercise duration of the training object according to the physical status in real time.

5 Claims, 7 Drawing Sheets

(51) Int. Cl.
*A61B 5/00* (2006.01)
*A61B 5/0205* (2006.01)
*A61B 5/021* (2006.01)
*A61B 5/024* (2006.01)

(52) U.S. Cl.
CPC ............ *A61B 5/6895* (2013.01); *A61B 5/746* (2013.01); *A61B 5/021* (2013.01); *A61B 5/024* (2013.01); *A61B 5/0205* (2013.01); *A61B 5/02055* (2013.01); *A61B 5/6894* (2013.01); *A61H 2201/1215* (2013.01); *A61H 2201/5007* (2013.01); *A61H 2201/5071* (2013.01); *A61H 2205/10* (2013.01); *A61H 2230/065* (2013.01); *A61H 2230/305* (2013.01); *A61H 2230/425* (2013.01); *A61H 2230/505* (2013.01)

(58) Field of Classification Search
CPC .... A63B 2022/0652; A63B 2022/0051; A63B 2022/0682; A63B 22/0048; A63B 22/205; A61H 1/0255
USPC .................................. 601/23, 27, 32, 35, 36
See application file for complete search history.

(56) References Cited

U.S. PATENT DOCUMENTS

| | | | | |
|---|---|---|---|---|
| 2008/0300914 | A1* | 12/2008 | Karkanias | G16H 40/67 705/2 |
| 2011/0082397 | A1* | 4/2011 | Alberts | A63B 24/0087 601/26 |
| 2011/0294624 | A1* | 12/2011 | Burnfield | A63B 21/0058 482/7 |
| 2013/0333489 | A1* | 12/2013 | David | B62M 6/50 73/862.641 |
| 2013/0345025 | A1* | 12/2013 | van der Merwe | A63B 22/0605 482/7 |
| 2014/0100491 | A1* | 4/2014 | Hu | A63B 23/03541 601/27 |
| 2016/0166881 | A1* | 6/2016 | Ridgel | G16H 50/70 482/7 |
| 2017/0340920 | A1* | 11/2017 | Posio | G16H 20/70 |
| 2017/0347895 | A1* | 12/2017 | Wei | A61B 5/0537 |

* cited by examiner

SMART MEDICAL REHABILITATION DEVICE

This application claims priority to Chinese Application CN 201611026826.0, filed Nov. 17, 2016 and Chinese Application CN 201611025862.5, filed Nov. 17, 2016. The entirely of the aforementioned application is incorporated herein by reference.

BACKGROUND OF THE INVENTION

1. Technical Field

The present invention relates to rehabilitation medicines, and more particularly to a smart medical rehabilitation device.

2. Description of Related Art

Proper use of mechanical rehabilitation equipment is the most effective way to help the handicapped, such as the disabled, the elderly, and people with injury and disease to reintegrate into society, Mechanical rehabilitation equipment is thus a bridge through which the handicapped can go back to society, and therefore is significant to social stability and harmony. As proven by the practice, mechanical rehabilitation equipment is beneficial to enhance effects of rehabilitation and shorten the time required by rehabilitation.

Development of mechanical rehabilitation equipment involves the following procedures: identification of the object it serves, acquirement of data, design of mechanical structure, and finalization and formation of products. As to the product discussed herein, it is designed to serve people having lower-limb handicaps and thus problems with walking. In terms of acquirement of data, an advanced information processing technique based on images is adopted. In particular, joints at human lower limbs are labeled, so as to facilitate extraction of coordinates of crucial sites from the video images, thereby allowing plotting of a gait curve reflecting human normal exercise as the basis of mechanical design. As regards mechanical design, on the basis of available features of the crucial point coordinates, the types of mechanisms, such as chain drive, rod mechanism and cam mechanism, can be selected. Mechanical design algorithms may be used to further determine the sizes of individual mechanisms. Afterward, assembling and engineering options for the shafts are considered to select suitable bushes, rolling bearings, end caps and the like. In respect of finalization and formation of products, installation of the mechanisms is planned reasonably with consideration to engineer technology and human behavior, and local adjustment is to be performed, such as placement of the groove plate and the pedals on left and right sides, the altitudinal range of the saddle, the altitudinal adjustment of the handrail and so on.

SUMMARY OF THE INVENTION

In view of the shortcomings of the prior art, the present invention provides a smart medical rehabilitation device, comprising a driving unit, a linkage unit, a sensing unit and a rehabilitation evaluating unit that are mounted on a frame. The smart medical rehabilitation device is characterized in that:

the linkage unit has a link mechanism and a slide mechanism linked thereto, the slide mechanism is driven by the driving unit to slide along a groove plate, and the link mechanism is linked with the slide mechanism thus it moves to the corresponding position so that the slide mechanism assists a training object in performing lower limb rehabilitation training, and the rehabilitation evaluating unit evaluates the physical status and rehabilitation status of the training object according to the physiological information and exercise information of the training object collected by the sensing unit, and adjusts the exercise frequency and exercise duration of the training object according to the physical status in real time.

According to one preferred embodiment, the slide mechanism comprises a slider, a guide shaft, a connecting bulge and a groove plate, the connecting bulge is connected to the driving unit by means of a secondary chain drive mechanism and being driven to rotate by the driving unit, and at least two guide shafts being provided between the slider and the connecting bulge for guiding the slider to move along the groove plate.

According to one preferred embodiment, the link mechanism comprises a rocker and a link, the link being rotatably connected between the rocker and the slider, the link being shaped into a right trapezoid with pedals for the training object to pedal arranged at two ends of the hypotenuse thereof respectively, the slider making the pedal assist the training object in performing the lower limb rehabilitation training by driving one end of the link to move along the groove plate.

According to one preferred embodiment, the connecting bulge is provided with a linear bearing at where it contacts at least one said guide shaft, and the guide shaft performs linear movement with respect to the connecting bulge as the slider moves along the groove plate.

According to one preferred embodiment, a fixing point of the pedal is connected to two ends of the link through at least two connecting rods so as to form a stable triangular structure;

the first connecting rod has its one end rotatably connected to the link and the rocker, and has its opposite end connected to the fixing point of the pedal;

the second connecting rod has its one end rotatably connected to the link and the slider, and has its opposite end connected to the fixing point of the pedal;

the first connecting rod, the second connecting rod, and the link have a length ratio of 5.4337:1.6957:4.2743; and the first connecting rod and the pedal have a plane included angle of 85 degrees.

According to one preferred embodiment, two said linkage units are symmetrically provided at two ends of the frame and connected to the driving unit through the symmetrically, provided secondary chain drive mechanisms, and a motor in the driving unit drives a major shaft whose gears at its two ends are connected to the secondary chain drive mechanisms, respectively, to rotate through the primary chain drive mechanism, thereby making the linkage units link to move in the driving frequency of the driving unit.

According to one preferred embodiment, the groove plate is centrally provided with a minor shaft that passes through a retaining plate of the groove plate, wherein the minor shaft has its one end transmissively connected to the secondary chain drive mechanism, and has its opposite end connected to the connecting bulge, so that the connecting bulge is driven by the secondary chain drive mechanism to rotate in the driving frequency.

According to one preferred embodiment, the sensing unit collects the physiological information, lower limb exercise frequency, foot motion trajectory and exercise duration of the training object, and the rehabilitation evaluating unit evaluates the rehabilitation status of the training object according to the physiological information and lower limb exercise frequency of the training object, and the pressure data of the pedal from the feed of the training object, and the rehabilitation evaluating unit adjusts the exercise frequency of the pedals by adjusting the driving frequency of the driving unit according to the physiological information of the training object.

According to one preferred embodiment, the sensing unit at least comprises a pressure sensor and a location information sensor arranged on the pedal, and a physiological information sensor arranged around a handrail on the frame.

According to one preferred embodiment, the rehabilitation evaluating unit comprises a data-processing unit, an evaluating unit and a control unit, wherein the data-processing unit screens valid data from exercise data collected by the sensing unit, and sends the valid data to the evaluating unit, the evaluating unit evaluates the physiological status and rehabilitation status of the training object based on the valid data, and the control unit adjusts the exercise frequency and exercise duration of the training object based on the evaluation of the evaluating unit.

A limb rehabilitation training system, comprising a mechanical structure module and a function module, wherein the function module at least comprises a sensing unit, a mobile terminal and a data-processing cloud terminal;

the data-processing cloud terminal performs the first matching between at least pressure data and/or time data and/or travel data collected by the sensing unit and the expert data stored in the data-processing cloud terminal, and stores results of the matching in the data-processing cloud terminal;

the data-processing cloud terminal performs the second matching between the personal information data of the training object collected by the mobile terminal and the results of the first matching, stores the results of the second matching in the data-processing cloud terminal, and sends the expert data of the results of the second matching that at least comprises duration of each training session and/or number of training sessions per day and/or training cycle and/or exercise mileage and/or support provided by the pedal as a recommended rehabilitation training scheme to the mobile terminal.

According to one preferred embodiment, the first matching is the correlation matching between the expert data stored in the data-processing cloud terminal and the pressure data collected by the sensing unit and/or the correlation matching between the expert data stored in the data-processing cloud terminal and the time data collected by the sensing unit, and/or the correlation matching between the expert data stored in the data-processing cloud terminal and the travel data collected by the sensing unit, and results of the matching are stored in the data-processing cloud terminal.

According to one preferred embodiment, the second matching is the matching between the results of the first matching stored in the data-processing cloud terminal and the personal information data including at least the age, body height and body weight of the training object collected by the mobile terminal, and results of the second matching are stored in the data-processing cloud terminal and sent to the mobile terminal as the recommended rehabilitation training scheme.

According to one preferred embodiment, the mobile terminal sends the pressure data, time data and travel data collected by the sensing unit to the data-processing cloud terminal for data update, and displays variations of the pressure data, time data and travel data to the training object by means of a list or a graph or diagram.

According to one preferred embodiment, the data-processing cloud terminal prepares a new recommended rehabilitation training scheme according to the updated pressure data, time data and/or travel data.

According to one preferred embodiment, the mobile terminal controls a motor in the mechanical structure module of the rehabilitation training system according to the recommended rehabilitation training scheme it receives, and affects the exercise mileage of the training object by adjusting the speed of the motor; and the mobile terminal displays the recommendations about the duration of each training session, the number of training sessions per day, the training cycle, the exercise mileage and the support provided by the pedal in the recommended rehabilitation training scheme to the training object by means of voice or a list.

According to one preferred embodiment, the expert data comprise a rehabilitation training program associated with the physiological data and/or body function data of the training object, the physiological data include the basic data of the training object such as body height, body weight and age, and the body function data include the support provided by the pedal, the exercise duration and the exercise mileage data for every exercise training course the training object has taken.

According to one preferred embodiment, the sensing unit comprises a pressure sensor, a time sensor, a velocity sensor, an amplification circuit, an A/D conversion circuit and a single-chip microcomputer, wherein the signal data collected by the pressure sensor, the time sensor and the velocity sensor is amplified by the amplification circuit and transmitted to the single-chip microcomputer through the A/D conversion circuit, and then the single-chip microcomputer performs preliminary processing on the data.

According to one preferred embodiment, the data-processing cloud terminal includes a data-processing unit and a rehabilitation database, wherein the data-processing unit serves to perform correlation matching on the data, and the rehabilitation database serves to store the data including the expert data, the data collected by the sensing unit, the data collected by the mobile terminal and the data of matching results generated during data matching.

According to one preferred embodiment, the mechanical structure module at least comprises: a groove plate for supporting a cam, a pedal for supporting the weight of the training object and driving the lower limb of the training object to move, a link for transmitting kinetic energy to the pedal, a rocker for supporting the link, a connecting bulge for driving a guide shaft to rotate, a linear bearing for supporting the guide shaft, the guide shaft for driving a slider to rotate, the slider for driving the link to operate, an axis pin for connecting the link and the slider, and a cam roller for making the slider move along a groove trajectory of the groove plate;

the pedal and the link are rigidly connected, while the link is hinged to the first rocker and the axis pin, respectively, the rocker is hinged to the frame, the connecting bulge is provided with two parallel columnar through holes, the linear bearing is received in the columnar through hole, the guide shaft passes through the linear bearing, the guide shaft and the slider are rigidly connected to each other, and the cam roller is rigidly connected to the connecting bulge through the axis pin;

the cam roller performs curved movement along the groove plate, as the curvature radius changes, the guide shaft performs linear movement with respect to the connecting bulge, the linear bearing is arranged in the connecting bulge for reducing mechanical wear between the guide shaft and the connecting bulge, thereby improving the service life.

The present invention has the following beneficial technical effects:

(1) The disclosure is developed using human normal exercise data collected in early experiments, and thus is highly adaptive and scientific. A patient can take rehabilitation training simply by walking following a human normal walking curve, so the rehabilitating effect can be improved and time required by rehabilitation can be reduced;

(2) The disclosure has a relatively extensive market prospect. By maximizing the use of standard parts, optimizing the stability of the frame and properly selecting engineering options for the shafts, the overall system is advantageously simple and reliable. It uses rolling bearings, linear bearings and cam rollers to minimize part wear and thereby enhancing the mechanical endurance of the product;

(3) The disclosure incorporates ergonomic consideration to optimize the mechanisms in terms of size, and altitudinal adjustment of the saddle as well as settings for the handrail, so as to ensure the rehabilitating effect while improving comfort in use; and (4) The disclosure can be used alone to assist people with lower limb problems in performing rehabilitation training, and can also work with other mechanical rehabilitation equipment to provide patients with more rehabilitation options.

Figure 1:
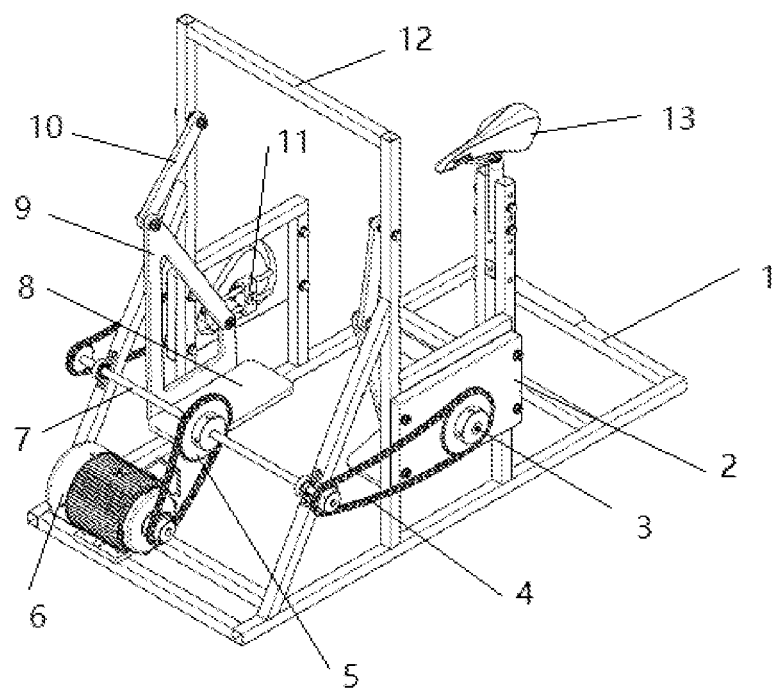
FIG. 1 is an overall structural drawing of the smart medical device of the present invention.

| Reference numerals | | |
|---|---|---|
| 1: frame | 2: groove plate | 3: minor shaft assembly |
| 4: the secondary chain drive mechanism | | |
| 5: the primary chain drive mechanism | | 6: motor |
| 7: major shaft | 8: pedal | 9: link |
| 10: rocker | 11: guide shaft assembly | 12: handrail |
| 13: saddle | 14: connecting bulge | 15: linear bearing |
| 16: guide shaft | 17: slider | 18: axis pin |

| Reference numerals | | |
|---|---|---|
| 19: cam roller | 20: end cap | 21: minor shaft |
| 22: bush | 23: rolling bearing | EG: the first connecting rod |
| DG: the second connecting rod | | GN: the third connecting rod |

DETAILED DESCRIPTION OF THE INVENTION

The invention as well as a preferred mode of use, further objectives and advantages thereof will be best understood by reference to the following detailed description of illustrative embodiments when read in conjunction with the accompanying drawings.

The objective of the present invention is to help patients having problems at their lower limbs and having difficulty in walking to rehabilitate themselves through physical training, thereby providing retarding exacerbation of any negative physical conditions. The disclosed device can also be used with other mechanical rehabilitation equipment to provide patients with more rehabilitation options.

Embodiment 1

As shown in FIG. 1, a medical rehabilitation device comprises a driving unit and a linkage unit mounted on a frame. The frame 1 is a structurally symmetrical stand formed by a plurality of bars connected together. The frame 1 comprises a rectangular support and a U-shaped support perpendicular to and connected to the rectangular support. The U-shaped support is located at the middle part of the rectangular support. The U-shaped support comprises two vertical rods perpendicular to the rectangular support and a horizontal rod parallel to the plane where the rectangular support rests on. The horizontal rod is connected between the two vertical rods. Two oblique rods are connected between the vertical rods of the U-shaped support and the corresponding rectangular support, so that the two oblique rods, the two vertical rods, and the rectangular support jointly form two stable triangular structures at two sides of the frame, respectively. The frame 1 is made of industrial aluminum profiles. In particular, plural industrial aluminum profiles are welded and screwed together. Its section assembly allows length adjustment of aluminum profiles and endows the product with high stability and good operability.

Two said linkage units are symmetrically provided at two sides of the frame and connected to the driving unit through the symmetrically arranged secondary chain drive mechanisms, and a driving device in the driving unit drives a major shaft whose gears at its two ends are connected to the secondary chain drive mechanisms, respectively, to rotate through the primary chain drive mechanism, thereby making the linkage units linked to move in the driving frequency of the driving unit.

The linkage units are located at two sides of the U-shaped support that is at the middle part of the frame. The linkage units comprise a first linkage unit arranged at one side of the frame 1, and a second linkage unit arranged at the opposite side of the frame. Since the first linkage unit and the second linkage unit are structurally identical, they are hereinafter each referred to as the linkage unit for succinctness.

Figure 2:
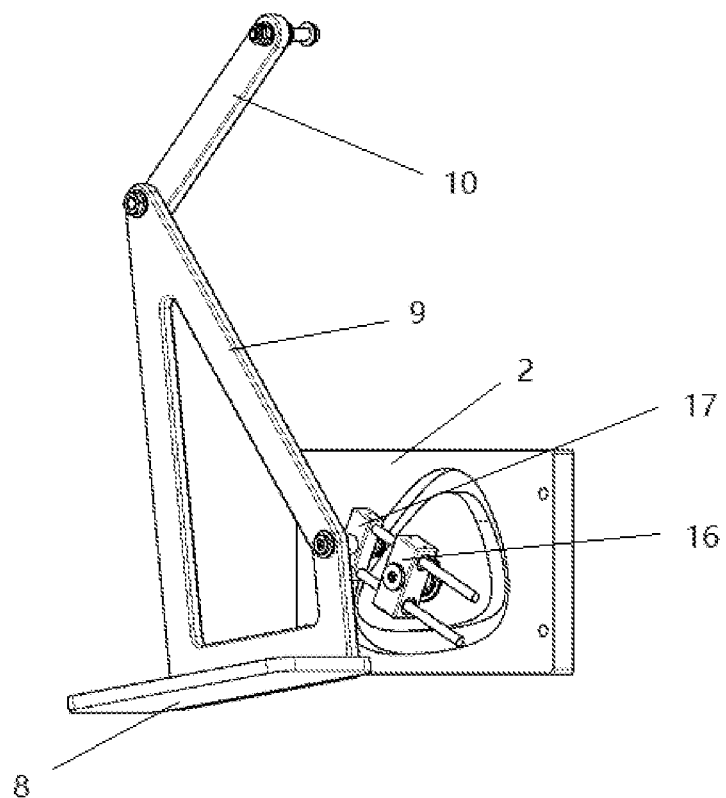
FIG. 2 is a structural schematic drawing showing a linkage unit in the smart medical device of the present invention.

As shown in FIG. 2, the linkage unit comprises a link mechanism and a slide mechanism linked thereto so that the slide mechanism can be moved together with the link mechanism. The link mechanism comprises a rocker 10 and a link 9. The rocker 10 has its one end rotatably connected to a vertical rod of the U-shaped support through a pivot, and has its opposite end rotatably connected to the link 9. The link 9 is rotatably connected between the rocker 10 and the slider 17. The link 9 is in the shape of a right trapezoid. The hypotenuse of the right trapezoid has its one end connected to one end of the rocker 10 and the opposite end connected to the slider 17, wherein one end of the hypotenuse that connects to the baseline is rotatably connected to one end of the rocker 10, the other end of the hypotenuse that connects to the topline is rotatably connected to the slider 17. The height between the topline and the baseline is provided with a pedal 8 for a training object to pedal.

Figure 6:
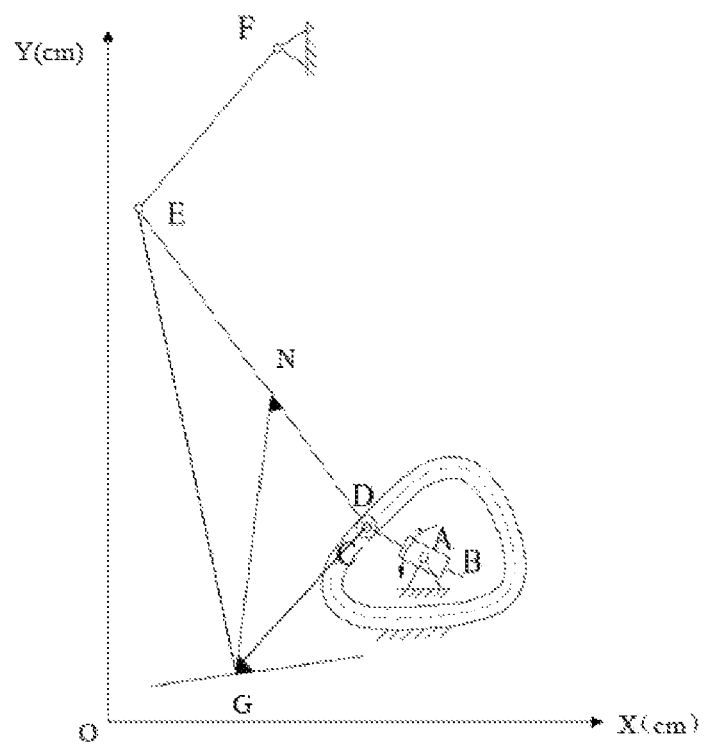
FIG. 6 is another structural drawing of the linkage unit of the smart medical device.

Preferably, as shown in FIG. 6, the pedal 8 has its fixing point connected to two ends of the link 9 through at least two connecting rods to form a stable triangular structure. The link 9 is hinged to the rocker 10 and the axis pin 18 on the slider 17. The rocker 10 is connected to the frame 1 by means of a hinge. The fixing point of the pedal 8 is connected to two ends of the link 9 through the first connecting rod EG and the second connecting rod DG; so as to form a stable triangular structure. Meanwhile, the link 9 is connected to the guide shaft assembly 11. The guide shaft assembly 11 is connected to the link 9 and the minor shaft assembly 3, respectively. The first connecting rod EG has its one end rotatably connected to the link 9 and the rocker 10, and has its opposite end connected to the fixing point of the pedal 8. The second connecting rod DG has its one end rotatably connected to the link 9 and the slider 17, and has its opposite end connected to the fixing point of the pedal 8. The first connecting rod EG, the second connecting rod DG, and the link 9 have a length ratio of 5.4337:1.6957:4.2743. The first connecting rod EG and the pedal 8 have a plane included angle of 85 degrees.

Preferably, the fixing point of the pedal 8 is connected to Point N at the middle part of the link 9 through the third connecting rod GN. The third connecting rod GN serves to evenly distribute force acting on two ends of the link 9, thereby extending the service life of the link 9.

Figure 3:
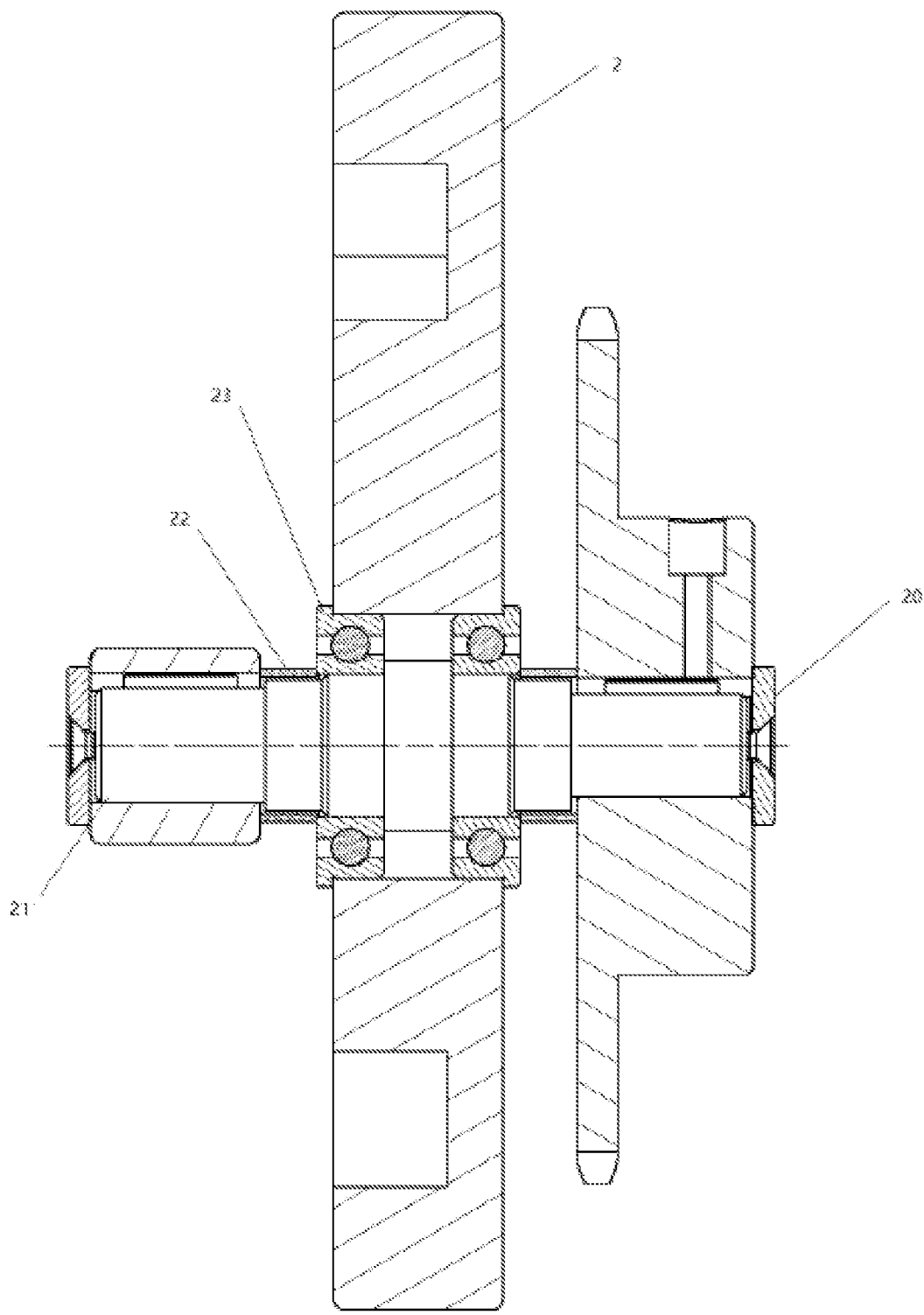
FIG. 3 is a cross-sectional view of a slide mechanism in the smart medical device of the present invention.

The slide mechanism comprises a slider 17, a guide shaft 16, a connecting bulge 14, and a groove plate 2. As shown in FIG. 3, the groove plate 2 is fixed to the frame 1 by means of screws and provided with a groove C on the inner side thereof. The groove plate 2 is designed according to statistics of human exercise physiology to meet the regular pattern of human lower limb movement, thereby helping training objects recover through comfortable training.

The retaining plate has its one end fixed to a vertical rod of the U-shaped support, and has its opposite end fixed to a retaining plate support that is parallel to the vertical rod. The retaining plate is provided with a minor shaft assembly 3 that positionally corresponds to the center of the groove plate 2 and passes through the retaining plate for transmission of kinetic energy. The minor shaft assembly 3 comprises a minor shaft 21 and a rolling bearing 23. Preferably, the groove plate 2 is provided with a columnar through hole. The rolling bearing 23 is received in the through hole of the groove plate 2, and is rigidly connected to the groove plate 2. The minor shaft 21 passes through the rolling bearing 23. The minor shaft 21 is rotatably connected to the center of the groove plate 2 through the rolling bearing 23. The minor shaft 21 has its one end transmissively connected to the secondary chain drive mechanism 4, and has its opposite end fixedly connected to the connecting bulge 14. The connecting bulge 14 is driven by the secondary chain drive mechanism 4 to rotate in the driving frequency. The minor shaft 21 has its two ends each provided with an end cap 20 for protection. A bush 22 is mounted around and protects the minor shaft 21 at its segment that is exposed to the air. Preferably, the rolling bearing 23 in the minor shaft assembly 3 has its two ends fixed to the bush 22 by means of shoulders. The minor shaft 21 has its two ends capped with the end cap 20 for axial reinforcement.

Figure 4:
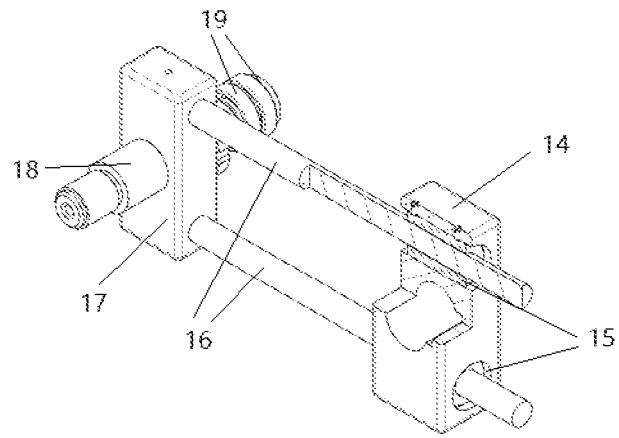
FIG. 4 is a structural drawing of a slide mechanism in the smart medical device of the present invention.

As shown in FIG. 4, the slider 17 at its one end contacting the groove plate 2 is provided with a cam roller 19. The slider 17 slides along the groove plate 2 through the cam roller 19. The slider 17 has its opposite end provided with an axis pin 18 that is rotatably connected to the hypotenuse of the link 9. The slider 17 is connected to the link 9 through the axis pin 18. At least two guide shafts 16 are arranged between the slider 17 and the connecting bulge 14 for guiding the slider 17 to move along the groove plate 2. The connecting bulge 14 at where it contacts at least one of the guide shafts 16 is provided with a linear bearing 15. Preferably, the connecting bulge 14 is provided with two columnar through holes that are parallel to each other, and the linear bearings 15 are received in the columnar through holes. The guide shafts 16 pass through the linear bearings 15. The guide shafts 16 and the slider 17 are rigidly connected. The cam roller 19 performs curved movement along the groove plate 2. As the curvature radius varies, the guide shafts 16 perform linear movement with respect to the connecting bulge 14 as the slider 17 moves along the groove plate 2, thereby reducing part wear and improving mechanical endurance. That is, the connecting bulge 14 is connected to the driving unit through the secondary chain drive mechanism 4 and rotates when being driven by the driving unit. The slider 17 makes the pedals 8 guide a training object to perform lower limb rehabilitation training by driving one end of the link 9 to move along the groove plate 2. Preferably, the number of guide shafts 16 is not limited to two, and may be three or more.

The driving unit is located at the front end of the frame 1. The driving unit comprises a motor 6, a major shaft 7, a primary chain drive mechanism 5 and a secondary chain drive mechanism 4. The connecting bulge 14 is connected to one end of the secondary chain drive mechanism 4 through the minor shaft 21. The secondary chain drive mechanism 4 has its opposite end transmissively connected to one end of the major shaft 7. Preferably, the primary chain drive mechanism 5 and the secondary chain drive mechanism 4 are both drive chains. The major shaft 7 has its two ends each provided with a gear mechanism engaged with the drive chain. Alternatively, the major shaft 7 is fixed to the frame 1 through two rolling bearings. The major shaft 7 has its two ends linked through the secondary chain drive mechanism, so as to transmit the kinetic energy it receives to the minor shaft assemblies at the two sides of the frame 1. Preferably, the major shaft 7 is centrally provided with a gear mechanism that is transmissively connected to the primary chain drive mechanism 5. The primary chain drive mechanism 5 has its two ends connected to the gear mechanism and the motor 6, respectively. The motor 6 transmits its kinetic energy to the major shaft 7 through the primary chain drive mechanism 5. The motor 6 is a servo motor that can perform adjustment according to feedback. The motor 6 provides power to drive forward and rearward rotation. The secondary chain drive mechanism 4 and the major shaft 7 split and deliver the power to linkage units at two sides of the frame for improved precision and transmission efficiency. The exercise frequency of the linkage unit is controlled by the driving unit and is consistent with the driving frequency of the driving unit.

Figure 5:
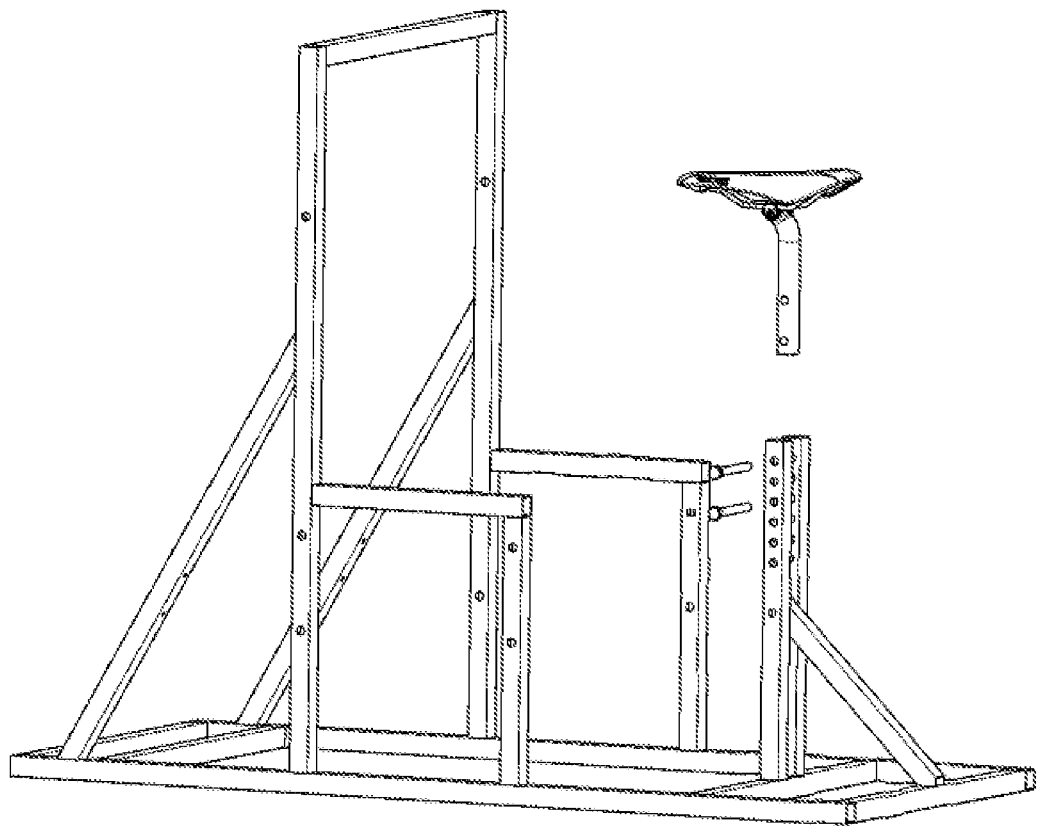
FIG. 5 is a schematic drawing showing a frame and a saddle of the smart medical device.

As shown in FIG. 5, the frame 1 is provided with a saddle 13 that is adjustable in terms of altitude. The saddle 13 is located at one end of the frame 1, and is connected to one prop of the frame 1 while positionally corresponding to the driving unit. The saddle 13 is positioned mainly by screw bolts engaged with holes formed on industrial aluminum profiles at different altitudes and holes at the lower end of the saddle 13, so as to improve the body comfort while ensuring rehabilitation results. In use, the screw bolts are screwed into the holes at different altitudes according to body comfort, and the altitude of the saddle altitude is thus set. The saddle is located according to human physiological features, so as to allow training objects to sit thereon comfortably and stably. The horizontal rod of the U-shaped frame of the frame 1 acts as a handrail 12 and is provided with a friction device, which prevents a training object from losing his/her balance by contacting the metal directly, thereby helping the training object to get his/her limbs stable and balanced. For example, a sleeve with a grained surface may be mounted around the handrail 12. A training object sitting in the saddle 13 can thus has his/her upper limbs rested on the handrail 12 to keep his/her body balanced. The training object at the same time can place his/her lower limbs on the corresponding pedals 8, respectively, and then get ready to perform lower limb rehabilitation training in the driving frequency of the driving unit. After the training object sits down with his/her lower limbs placed on the pedals and hands on the handrail 12, he/she can turn on the switch to activate the motor 6. The motor 6 provides forward and rearward rotational power within a predetermined angular range, so as to provide power to the linkage units and drive the linkage units to make the pedals 8 move along ergonomically designed foot motion trajectories.

Preferably, the pedals in the two units are a first pedal and a second pedal. The first pedal and the second pedal are designed to move along the same rotational direction. The first pedal and the second pedal always have a constant positional difference therebetween. For example, the first pedal and the second pedal are always 180 degrees away from each other. The driving frequency of the motor 6 is adjusted according to the exercise frequency fed back by the rehabilitation evaluating unit.

The present invention provides a smart medical rehabilitation device, which comprises a driving unit, a linkage unit, a sensing unit and a rehabilitation evaluating unit all mounted on a frame.

The sensing unit collects exercise data generated when a training object takes exercise. The exercise data include the foot sole loading data, the lower limb exercise frequency, the exercise duration, the physiological information data and the foot motion trajectory of the training object. The physiological information data include the variation in physiological parameters such as body weight, heart beat frequency, blood pressure, body temperature, pulse, breath frequency and so on.

The rehabilitation evaluating unit evaluates the rehabilitation status of the training object according to the physiological information, the lower limb exercise frequency of the same, and the pressure data of the pedals from the feet of the training object.

Figure 8:
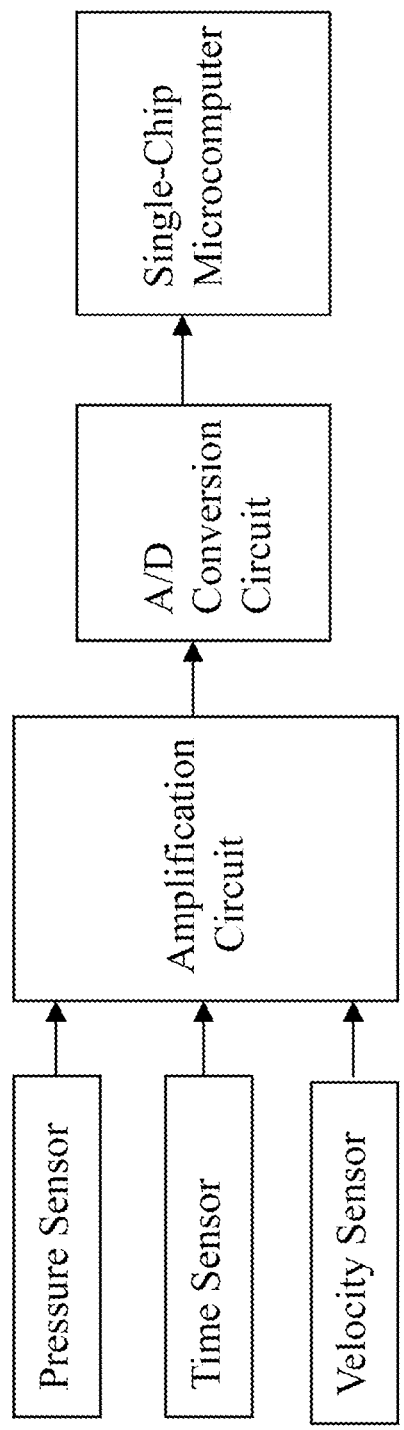
FIG. 8 is a connection management diagram of a sensing unit of the smart medical device.

As shown in FIG. 8, the sensing unit at least comprises a pressure sensor and a location information sensor arranged on the pedal, and a physiological information sensor arranged around a handrail on the frame.

Preferably, the pedal 8 is provided with at least one pressure sensor. The pressure sensor monitors the foot sole loading of the training object, for measuring the size of the support the pedal gives to the training object. The location information sensor monitors the moving trajectory of the pedal 8, thereby monitoring the foot motion trajectory and exercise frequency of the training object. The handrail 12 is provided with at least one physiological information sensor, which may be a heart rate sensor, a body temperature sensor, or a blood pressure sensor. Preferably, the sensing unit further comprises a pulse sensor installed on a wrist band.

In the process where a training object performs lower limb rehabilitation training, the sensing unit collects the body weight, the blood pressure, the heart beat, the temperature, the exercise frequency, the foot motion trajectory and other relevant data of the training object. Specifically, when the training object has his/her feet placed on the pedals 8 and stands stably with the support of the handrail, the pressure sensor on the pedal 8 records the body weight of the training object. After the training object sits down, the pressure sensor on the pedal 8 monitors pressure variation between the training object and the pedal 8 throughout the training of the training object. The location information sensor on the pedal monitors the foot motion trajectory and exercise frequency of the training object. When deviation is observed in the foot motion trajectory, it means that some mechanism(s) in the linkage unit has/have loosened connection or failure. The temperature sensor, the heart rate sensor and the blood pressure sensor on the handrail 12 monitor the body temperature variation, the heart beat variation and the blood pressure variation of the training object. The pressure sensor on the saddle 13 monitors the bottom pressure variation of the training objects after he/she sits down.

The rehabilitation evaluating unit adjusts the exercise frequency of the pedals based on the physiological information of the training object by adjusting the driving frequency of the driving unit, so as to ensure optimal rehabilitating effects.

The rehabilitation evaluating unit may be installed on either the frame 1 or the handrail 12, and performs data transmission in a wired or wireless manner. Alternatively, it may be installed in the smart mobile terminal to perform data transmission wirelessly. The rehabilitation evaluating unit stores therein foot motion trajectories and exercise frequencies obtained through scientific computation. When a training object performs his/her lower limb rehabilitation training with the device for the first time, the rehabilitation evaluating unit receives the exercise frequency, the foot motion trajectories and the physiological information data transmitted by the sensing unit, and compares the physiological information to the standard physiological information data corresponding to the exercise frequency. If the difference between the physiological information data and the standard physiological information data does not exceed the predetermined tolerance, the exercise frequency of the training object is not adjusted. If the difference between the physiological information data and the standard physiological information data is great, the rehabilitation evaluating unit sends a command to the driving unit to adjust the driving frequency of the motor 6, thereby indirectly adjusting the exercise frequency of the training object, so as to match the exercise frequency with the physiological information data, thereby providing the training object with optimal effects of his/her lower limb rehabilitation training.

In one instance, the training object belongs to a special group, such as a group of children. The rehabilitation evaluating unit adjusts the lower limb exercise frequency of the training object based on the pressure data related to the training object standing on the pedal 8 and the physiological information data of the training object, thereby optimizing lower limb rehabilitation training for children or for other special training object groups.

In one instance, the training object is a robot. The rehabilitation evaluating unit readjusts the exercise frequency and saddle altitude based on the pressure data related to the training object standing on the pedal 8 and the foot motion trajectory. When the training object is sitting on the saddle, and the pressure observed by the pressure sensor of the pedal 8 vanishes at the same time, it is proved that the smallest distance between the saddle and the pedal exceeds the lower limb length of the training object. The rehabilitation evaluating unit thus adjusts the distance among the saddle 13, the handrail 12 and the pedals 8, until all the data and exercise frequency throughout the current exercise session of the training object enter the normal range.

Preferably, the rehabilitation evaluating unit evaluates the health of the training object based on the physiological information data and exercise frequency of the training object collected by the sensing unit. The exercise frequency and the exercise duration are adjusted based on the physiological information data of the training object. When the physiological information data of the training object show abnormality, the rehabilitation evaluating unit stops guiding the training object to perform lower limb rehabilitation training, and returns the training object to a standard sitting posture. Preferably, the rehabilitation evaluating unit comprises an alarm unit. When the physiological information data of the training object show abnormality, the alarm unit gives out alarm information in the form of acoustic alarms, light alarms and/or any combination thereof.

Preferably, the rehabilitation evaluating unit comprises a data-processing unit, an evaluating unit and a control unit, wherein the data-processing unit screens valid data from exercise data collected by the sensing unit, and sends the valid data to the evaluating unit, the evaluating unit evaluates the physiological status and rehabilitation status of the training object based on the valid data, and the control unit adjusts the exercise frequency and exercise duration of the training object based on evaluation of the evaluating unit.

The data-processing unit screens valid data from the exercise-related data collected by the sensing unit, and sends the valid data to the evaluating unit. The data collected by the various sensors of the sensing unit are not necessarily valid, and may include some error data outside the tolerance. The data-processing unit screens the data transmitted by the data acquiring unit, and removes those outside the tolerance, so as to get accurate valid data and send them to the evaluating unit.

The evaluating unit evaluates the physical status and shoulder movement curve of the training object based on the valid data. The evaluating unit evaluates the physical status of the training object based on the valid data it receives. For example, if the training object has an increasing heart beat frequency during his/her standing training and it turns out that his/her heart beat frequency exceeds a normal range, the evaluating unit instructs the control unit to decrease the exercise frequency, thereby allowing the heart beat frequency of the training object to come back to the normal frequency. The evaluating unit stores therein physiological information data obtained through scientific computation and exercise frequencies matching with them. When a training object performs his/her lower limb rehabilitation training with the disclosed device for the first time, the evaluating unit compares the physiological information data of the training object to the stored standard physiological information data. If the difference between the physiological information data and the standard physiological information data does not exceed the tolerance, the exercise frequency of the training object is not adjusted. If the difference between the physiological information data and the standard physiological information data is great, the rehabilitation evaluating unit sends a command to the driving unit to adjust the driving frequency of the motor 6, thereby indirectly adjusting the exercise frequency of the training object, so as to match the exercise frequency with the physiological information data, thereby providing the training object with optimal effects of his/her lower limb rehabilitation training.

The control unit is connected with the driving unit and the linkage units. The control unit corrects the exercise frequency, the exercise duration of the training object, and the position of the saddle 13 based on the evaluation made by the evaluating unit.

Preferably, the rehabilitation evaluating unit is an electronic module, and may be located arbitrarily on the frame 1. Preferably, the data-processing unit and the evaluating unit in the rehabilitation evaluating unit are installed in the smart mobile terminal. The control unit is located arbitrarily on the frame 1. The data acquiring unit sends the collected data to the data-processing unit on the smart mobile terminal in a wireless manner. For example, the data acquiring unit sends the data to the data-processing unit through wireless transmission technologies such as Bluetooth, WiFi, ZigBee, iBeacon or the like. The evaluating unit performs evaluation based on the valid data sent by the data-processing unit, and sends modulating commands to the control unit wirelessly. For example, the evaluating unit sends the data to the control unit through wireless transmission technologies such as Bluetooth, WiFi, ZigBee, iBeacon or the like.

According to one preferred aspect, the pressure sensor, temperature sensor, heart rate sensor, blood pressure sensor, and breath frequency sensor of the data acquiring unit are provided with an EnOcean module that provides energy. The EnOcean module converts the thermal energy and mechanical energy of the training object into electric power to power the sensors.

Embodiment 2

The present embodiment further explains Embodiment 1, and what has been discussed related to Embodiment 1 is omitted herein.

As shown in FIG. 6, the connecting bulge A corresponds to the connecting bulge 14. In the drawing, the rod B corresponds to guide shaft 16, and the slider D corresponds to slider 17. In the drawing, the groove C corresponds to the groove structure on the groove plate. The groove C is a loop-like groove with a roughly triangular structure. The groove C is designed according to foot movement curve information collected in experiments and conforms with sports engineering trajectory related to human walk. The connecting bulge A is driven by the minor shaft to rotate anticlockwise. The slider D moves along the groove C based on the connecting bulge A in response to the kinetic energy transmitted by the guide shaft B. As the curvature radius varies, the rod B moves linearly with respect to the connecting bulge A. The slider D when rotating drives the rod ED it is hinged to perform reciprocating movement along the groove C, thereby making the pedal 8 perform reciprocating movement.

One end of the rocker 10 and a vertical rod of the U-shaped support are rotatably fixed to the Point F at the center of the hinge. The opposite end of the rocker 10 is rotatably connected to the one end of the link 9 at Point E. The opposite end of the link 9 is rotatably connected to the slider 17 at Point C.

The auxiliary pivot point of the crank DB of the groove plate 2 is connected to the connecting bulge 14 at Point A. The slider 17 and the cam roller 19 are connected at Point D. The pedal 8 and the link 9 are fixedly connected at Point G. The dimensional proportion of the linkage unit is herein described with reference to the linkage unit shown in FIG. 6. Assuming that O is the origin, and the horizontal direction represents the X axis, while the vertical direction represents Y axis, a Cartesian coordinate system is so established. The fixed center Point A has its coordinates as (9.0000, 2.8593), and Point F has its coordinates as (7.2664, 8.6082). The rocker length EF=2.3523 cm. The link length DE=4.2743 cm. The terminal E of the rocker 10 is away from the pedal fixing point G in a distance of EG=5.4337 cm. The center of the cam roller 19 is away from the fixing point of the pedal in a distance of DG=1.6957 cm. The pedal 8 is fixed to the link 9 so that the plane where the pedal 8 rests on and the line EG jointly include an angle of 85 degrees. The orbit coordinates of the groove plate 2 at least comprise nine point coordinates. In addition to the nine sets of coordinates for defining the orbit coordinates of the groove plate 2 of the present invention easily, there are some more coordinate points that facilitate smoother movement of the cam roller 19 among the nine coordinate points. Since the trajectory of the groove plate 2 is not highly demanded in terms of precision, rounding off and fine tuning are allowable to ensure smooth movement of the cam roller 19 along the groove plate 2. The groove plate 2 is preferably defined with nine coordinate points, as shown in Table 1.

TABLE 1

| | Coordinate number | | | | | | | | |
|---|---|---|---|---|---|---|---|---|---|
| | 1 | 2 | 3 | 4 | 5 | 6 | 7 | 8 | 9 |
| X (cm) | 10.0966 | 9.8138 | 9.4072 | 9.1915 | 8.9212 | 8.6629 | 7.9973 | 7.5225 | 8.2912 |
| Y (cm) | 2.6041 | 3.6807 | 4.0818 | 4.0651 | 3.8782 | 3.6400 | 3.0327 | 2.4986 | 2.4346 |

Since individual training objects are similar yet different in, for example, the body height, the upper limb length and the lower limb length, the orbit coordinates of the groove plate 2 may be slightly different from the orbit coordinates shown in the present invention, thereby allowing the disclosed smart medical device to adapt to different individuals.

In the present invention, the linkage units may be scaled up or down according to the structure of the linkage units shown in FIG. 6, and installed on smart medical devices of different sizes, so as to meet different training/medical needs of adults, children and robots of various sizes.

Embodiment 3

The present embodiment further improves Embodiments 1 and 2, and what has been discussed related to Embodiments 1 and 2 is omitted herein.

Figure 7:
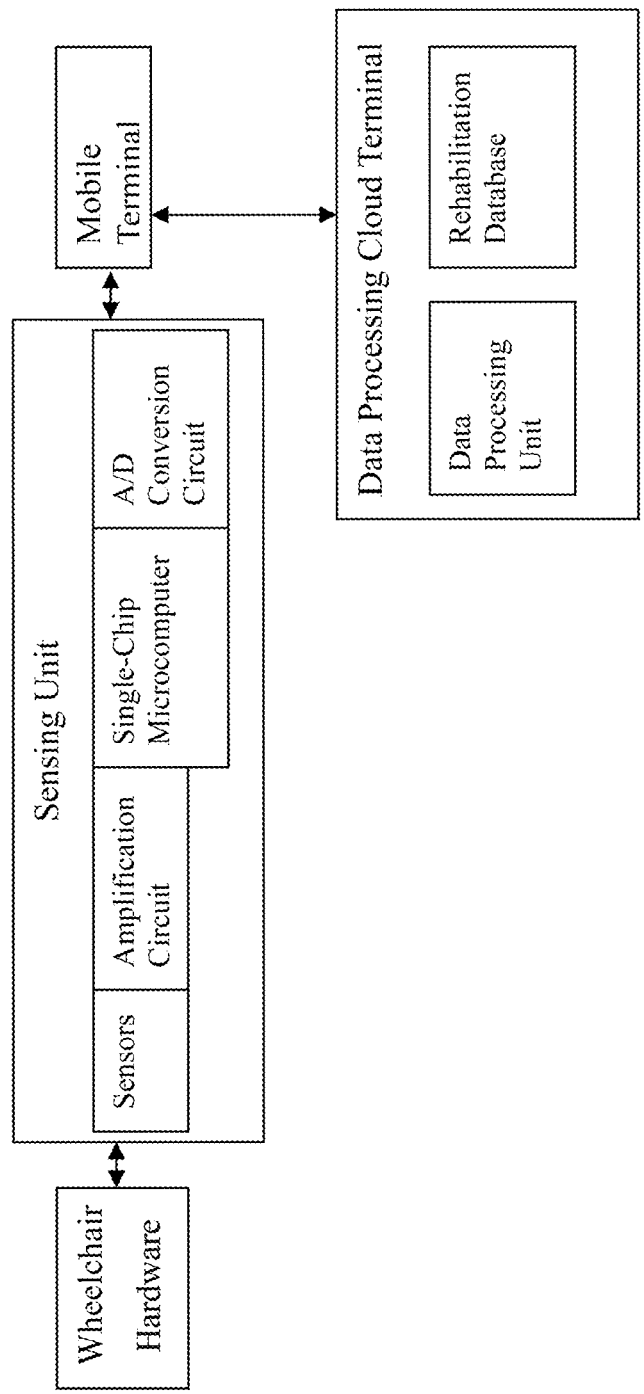
FIG. 7 is a diagram showing connection between function modules of the present invention.

The present embodiment provides a rehabilitation training system. As shown in FIG. 7, the rehabilitation training system comprises a mechanical function module composed of a sensing unit, a mobile terminal, and a data-processing cloud terminal. The data-processing cloud terminal includes a data-processing unit and a rehabilitation database, in which the data-processing unit serves to perform correlation matching on the data, and the rehabilitation database serves to store the data including the expert data, the data collected by the sensing unit, the data collected by the mobile terminal and data of matching results generated during data matching.

During a rehabilitation training of a training object, at least one set of monitoring data of the training object collected by the sensing unit is sent to the data-processing cloud terminal through the mobile terminal, and the personal information data of the training object collected by the mobile terminal are sent to the data-processing cloud terminal, so that the data-processing cloud terminal performs data processing analysis on the monitoring data and the personal information data it receives, and accordingly provides a recommended scheme for the subsequent training of the training object. The present invention thereby provides training object-specific training. In addition, human-machine interaction is established by the sensing unit, the mobile terminal and the data-processing cloud terminal, thereby providing a rehabilitation training program to a training object in view of his/her rehabilitation status and allowing real-time adjustment.

As shown in FIG. 8, the sensing unit comprises a pressure sensor, a time sensor, a velocity sensor, an amplification circuit, an A/D conversion circuit, and a single-chip microcomputer.

The velocity sensor is installed on the joint between the pedal and the rocker at one side of the frame 1, for measuring directional variation in the movement of the pedal. Every time the pedal completes a round of directional plus-minus variation, a count is generated. The exercise mileage of the training object can thus be calculated through the counts and the travel of a single reciprocating movement of the pedal. The pressure sensor may be a pressure sensor LLB450 from Futek, the US, with a range of 13344 N and a rated output of 2 mV/V. The sensor has an electrical signal it collects amplified by the amplification circuit and transmits the signal to the A/D conversion circuit. The signal is then input to the single-chip microcomputer for preliminary processing, and the single-chip microcomputer sends the processed data to the mobile terminal.

The sensing unit collects pressure data about the pressure the training object applies to the pedals using the pressure sensor. The sensing unit collects time data about how long the training object takes the training using the time sensor. The sensing unit collects mileage data about mileage corresponding to the lower limb exercise of the training object using the velocity sensor. The data collected by these sensors are transmitted to the single-chip microcomputer through the amplification circuit and the A/D conversion circuit.

The single-chip microcomputer conducts preliminary analysis of the collected data. Then the single-chip microcomputer sends the preliminarily analyzed data to the mobile terminal. The training object thus can anytime check the exercise data collected by the sensing unit during his/her training at the exercise terminal. The mobile terminal sends the pressure data, time data and travel data collected by the sensing unit to the data-processing cloud terminal for data update, and displays variation of the pressure data, time data, and travel data to the training object by means of a list or a graph or diagram.

The mobile terminal receives the monitoring data of the training object collected by the sensing unit, collects the initial personal information data of the training object at the same time, and sends the monitoring data and the personal information data to the data-processing cloud terminal. The data-processing cloud terminal stores the data it receives into the rehabilitation database of the training object, and updates the historical data accordingly. The data-processing unit analyzes the physical data of the training object based on the updated rehabilitation information data, and provides further feedback about exercise recommendation.

The mobile terminal can also receive the feedback information from the data-processing cloud terminal and controls the training mechanism of the rehabilitation training system using the single-chip microcomputer according to the feedback data, thereby guiding the training object to finish the training. Preferably, the mobile terminal controls the motor 6 of the rehabilitation training system in terms of speed according to the feedback data using the single-chip microcomputer, thereby controlling the exercise mileage of the training object and helping them finish the training. The feedback information comprises recommendation for duration of each exercise session for the specific training object, recommendation for exercise cycle, recommendation for exercise mileage, and recommendation for whether the legs of the training object can bear greater pressure or whether the training object needs to stand up from the saddle 13 and do exercise with only support from his/her own legs and the handrail. The mobile terminal displays the recommendations about the duration of each training session, the number of training sessions per day, the training cycle, the exercise mileage and the support provided by the pedal in the recommended rehabilitation training scheme to the training object by means of voice or a list.

The training object may use the mobile terminal to adjust the training program provided by data-processing cloud terminal according to his/her own properties, thereby setting his/her personalized training program. The data-processing cloud terminal collects the monitoring data transmitted by the mobile terminal and collected by the sensing unit and the personal information data collected by the mobile terminal, and processes and analyzes the data, thereby identifying at which training stage the recovery of the training object is. Then it feeds the training program of that stage back to the mobile terminal.

In the present invention, the data processing includes three parts. The first part involves recommending a rehabilitation training program based on the expert data stored in the rehabilitation database. The rehabilitation training program is a result of two-stage matching correlation performed by the data-processing cloud terminal between the data collected by the sensing unit/the data collected by the mobile terminal and the expert data. The first matching is the correlation matching between the expert data stored in the data-processing cloud terminal and the pressure data collected by the sensing unit and/or the correlation matching between the expert data stored in the data-processing cloud terminal and the time data collected by the sensing unit, and/or the correlation matching between the expert data stored in the data-processing cloud terminal and the travel data collected by the sensing unit, and results of the matching are stored in the data-processing cloud terminal. The second matching is the matching between the results of the first matching stored in the data-processing cloud terminal and the personal information data including at least the age, body height, and body weight of the training object collected by the mobile terminal, and results of the second matching are stored in the data-processing cloud terminal and sent to the mobile terminal as the recommended rehabilitation training scheme. The expert data comprise a rehabilitation training program associated with the physiological data and/or body function data of the training object. The physiological data include the basic data of the training object such as body height, body weight, and age. And the body function data include support provided by the pedal, exercise duration and exercise mileage data for every exercise training course the training object has taken.

The data-processing cloud terminal comprises a data-processing unit. The data-processing unit processes the monitoring data of the training object and personal information transmitted by the mobile terminal to normalize the monitoring data and the personal information data into basic physiological data that include the body height, the body weight and the age of the training object, and the body function data that include the support provided by the device, the exercise duration and the exercise mileage for each exercise training session of the training object. The rehabilitation database of the data-processing cloud terminal defines which training stage the recovery of the training object is depending on the physiological data and body function data of the training object, and provides the training object with different recommended training programs for different recovery stages, wherein the training program comprises duration of each training session, support provided by the device, the number of training sessions to be fulfilled per day, the interval between two successive training sessions and mileage for every training session.

The second part relates to real-time adjustment of the rehabilitation training program. Based on the data collected by the device's sensing unit, the recovery of the training object is monitored. If it is found that the training object exerts increasing force at his/her feet, the support to be provided by the saddle 13 or the handrail 12 is adjusted, and the support from the pedals is updated to the training program for the training object. Likewise, the data-processing cloud terminal may update the data about duration of each training session, the number of training sessions to be fulfilled per day or the interval between two successive training sessions.

The third part involves using machine learning or the like to realize a personalized training update. The data-processing cloud terminal keeps rehabilitation training statuses of different training objects. After rehabilitation training data are collected from a large group of people, a machine learning algorithm is performed on the rehabilitation training data of all training objects, and cluster analysis is carried out, wherein a similarity measurement on which clustering is based is determined using variables such as patients' body height, body weight, age, training amount, and percentage of force exerted in every training session. By clustering people with similarity, accurate personalized rehabilitation training programs may be formulated for different training objects. A personalized rehabilitation training program may specify duration of each training session, support provided by the device, the number of training sessions to be fulfilled per day, the interval between two successive training sessions, and exercise mileage for each session.

It should be noted that the above specific embodiments are exemplary, persons skilled in the art can devise various solutions under the inspiration of the disclosed content of the present invention, and the solutions also belong to the disclosed scope of the present invention and fall into the protection scope of the present invention. Persons skilled in the art shall understand that the specification and its drawings of the present invention are exemplary and do not limit the claims. The protection scope of the present invention is limited by the claims and its equivalents.

What is claimed is:

1. A limb rehabilitation training system, comprising:
a mechanical structure module, comprising:
   a driving unit; and
   a linkage unit arranged on a frame; and
a function module, comprising:
   a sensing unit that collects body function data, wherein the body function data comprises pedal pressure, exercise duration, and exercise mileage;
   a mobile terminal; and
   a data-processing cloud terminal comprising a data-processing unit and a rehabilitation database,
wherein the sensing unit comprises a single-chip microcomputer, a pressure sensor that collects the pedal pressure data, a time sensor that collects the exercise duration data, a velocity sensor that collects the exercise mileage data, an amplification circuit and an A/D conversion circuit that amplifies and transmits body function data collected by the pressure, time and velocity sensors to the single-chip microcomputer, wherein the single-chip microcomputer sends the body function data to the mobile terminal,
wherein the mobile terminal collects physiological data of the training object and sends both the body function data and the physiological data to the data-processing cloud terminal, wherein the physiological data include body height, body weight, and age of the training object, and
wherein the data-processing cloud terminal performs a first matching between data collected by the sensing unit, and expert data stored in the data-processing cloud terminal to provide a first rehabilitation training program, and stores the first rehabilitation training program in the data-processing cloud terminal; wherein the expert data comprise rehabilitation training programs associated with physiological data and/or body function data of training objects, and
wherein the data-processing cloud terminal performs a second matching between physiological data of the training object collected by the mobile terminal and the first rehabilitation training program to generate a second rehabilitation training program, stores the second rehabilitation training program in the data-processing cloud terminal, and sends the second rehabilitation training program to the mobile terminal as a recommended rehabilitation training scheme, wherein the second rehabilitation training program comprises a duration of each training session and/or a number of training sessions per day and/or a training cycle and/or an exercise mileage and/or support provided by a pedal,
wherein the mechanical structure module at least comprises: a groove plate for supporting a cam roller, the pedal for supporting the weight of the training object and driving the lower limb of the training object to move, a link for transmitting kinetic energy to the pedal, a rocker for supporting the link, a connecting bulge or driving a guide shaft to rotate, a linear bearing for supporting the guide shaft, the guide shaft for driving a slider to rotate, the slider for driving the link to operate, an axis pin for connecting the link and the slider, and the cam roller for making the slider move along a groove trajectory of the groove plate; wherein the pedal and the link are rigidly connected, while the link is hinged to the first rocker and the axis pin respectively, the rocker is hinged to the frame, the connecting bulge is provided with two parallel columnar through holes, the linear bearing is received in the columnar through hole, the guide shaft passes through the linear bearing, the guide shaft and the slider are rigidly connected to each other, and the cam roller is rigidly connected to the connecting bulge through the axis pin, and the cam roller performs curved movement along the groove plate, as the curvature radius changes, the guide shaft performs linear movement with respect to the connecting bulge, the linear bearing is arranged in the connecting bulge for reducing mechanical wear between the guide shaft and the connecting bulge, thereby improving the service life.

2. The rehabilitation training system of claim 1, wherein the first matching is a correlation matching between the expert data stored in the data-processing cloud terminal and the pressure data collected by the sensing unit.

3. The rehabilitation training system of claim 1, wherein the mobile terminal controls a motor in the mechanical structure module of the rehabilitation training system according to the recommended rehabilitation training scheme the mobile terminal receives, and affects the exercise mileage of the training object by adjusting the speed of the motor; and wherein the mobile terminal displays recommendations about the duration of each training session, the number of training sessions per day, the training cycle, the exercise mileage and the support provided by the pedal in the recommended rehabilitation training scheme to the training object by means of voice or a list.

4. The rehabilitation training system of claim 1, wherein the linkage unit has a link mechanism and a slide mechanism linked thereto, so that the slide mechanism can be moved together with the link mechanism, the slide mechanism is driven by the driving unit to slide along a groove plate, and the link mechanism is linked to move together with the slide mechanism thus the link mechanism moves to a corresponding position, so that the slide mechanism can assist the training object in performing lower limb rehabilitation training, and wherein the rehabilitation training system further comprises a rehabilitation evaluating unit which evaluates a physical status and rehabilitation status of the training object according to physiological information and exercise information of the same collected by the sensing unit, and adjusts an exercise frequency and exercise duration of the training object according to the physical status in a real-time manner.

5. The rehabilitation training system of claim 1, wherein the data-processing cloud terminal includes a data-processing unit and the rehabilitation database, wherein the data-processing unit serves to perform correlation matching on collected data, and the rehabilitation database serves to store the collected data comprising the first related expert data, the data collected by the sensing unit, the data collected by the mobile terminal and the data of matching results generated during the first data matching.

* * * * *